(12) United States Patent
Filikov

(10) Patent No.: US 7,117,102 B2
(45) Date of Patent: Oct. 3, 2006

(54) METHOD OF PREDICTION OF SOLUBILITY OF CHEMICAL COMPOUNDS

(75) Inventor: Anton Filikov, 55 Pitman Ave., Wakefield, MA (US) 01880

(73) Assignee: Anton Filikov, Wakefield, MA (US)

( * ) Notice: Subject to any disclaimer, the term of this patent is extended or adjusted under 35 U.S.C. 154(b) by 244 days.

(21) Appl. No.: 10/805,078

(22) Filed: Mar. 20, 2004

(65) Prior Publication Data

US 2004/0225451 A1  Nov. 11, 2004

Related U.S. Application Data

(60) Provisional application No. 60/455,955, filed on Mar. 20, 2003.

(51) Int. Cl.
*G06F 9/06* (2006.01)
(52) U.S. Cl. ............... 702/30; 702/22; 702/31; 702/32; 702/179; 702/183
(58) Field of Classification Search ............ None
See application file for complete search history.

(56) References Cited

U.S. PATENT DOCUMENTS 6,350,369 B1 * 2/2002 Lewis et al. ............ 205/777.5
6,957,151 B1 * 10/2005 Cheng et al. .................. 702/30
2002/0081232 A1 * 6/2002 Lewis et al. ............. 422/82.02
2003/0131015 A1 * 7/2003 Chen .......................... 707/100
2004/0197934 A1 * 10/2004 Bajorath et al. ............ 436/518
2005/0069911 A1 * 3/2005 Lee et al. ....................... 435/6

OTHER PUBLICATIONS

U.S. Appl. No. 60/455,955, filed Mar. 20, 2003, Anton Filikov.

* cited by examiner

*Primary Examiner*—Carol S. W. Tsai

(57) ABSTRACT

Descriptors of cohesive interactions in the solid state are calculated from a computational model of a solid state, i.e. from a small cluster of copies of the molecule of interest assembled using a molecular mechanics method. A model for predicting solubility is built using the cohesive interaction descriptors along with other descriptors useful for this purpose. Predicted solubility is computed for the compound of interest by computing the same descriptors and applying the solubility model. Explicit modeling of solid state allows to more accurately characterize cohesive interactions in solids, hence, more accurately predict solubility.

3 Claims, 2 Drawing Sheets

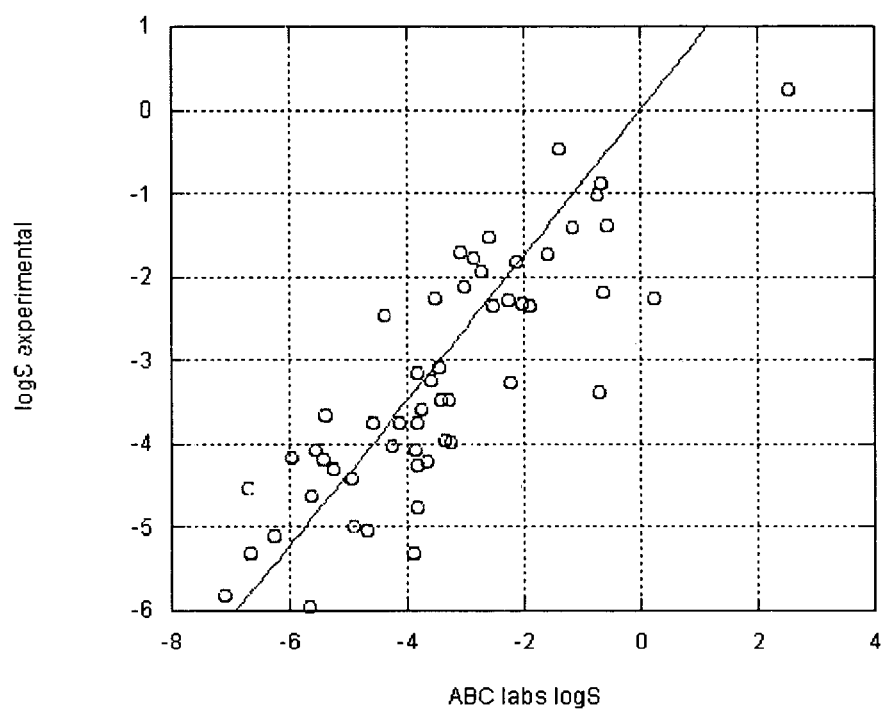
FIG. 1 Correlation of predicted and experimental logS values for the ACD method.

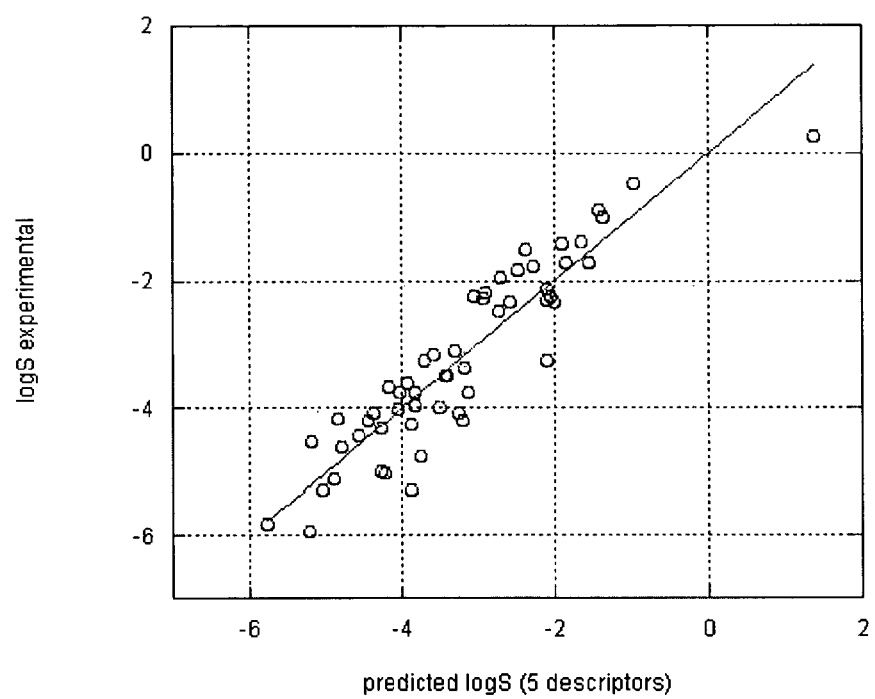
FIG. 2 Correlation of predicted and experimental logS values for the described method.

METHOD OF PREDICTION OF SOLUBILITY OF CHEMICAL COMPOUNDS

This application claims the benefit of the provisional application 60/455,955 filed Mar. 20, 2003.

REFERENCES CITED

J. Huuskonen, M. Salo, J. Taskinen, Aqueous Solubility Prediction of Drugs Based on Molecular Topology and Neural Network Modeling, J. Chem. Inf. Comput. Sci. 38 (1998) 450–456.

W. L. Jorgensen, E. M. Duffy, Prediction of Drug Solubility from Monte Carlo Simulations, Bioorg. Med. Chem. Lett. 10 (2000) 1155–1158.

F. Irmann, Eine einfache korrelation zwischen wasserloslichkeit und strukture von kohlenwasserstoffen und halogenkohlenwasserstoffen. Chem. Ing. Tech. 37 (1965) 789–798.

C. Hansch, J. E. Quinlan, G. L. Lawrence, Linear free energy relationship between partition coefficients and the aqueous solubility of organic liquids, J. Org. Chem. 33 (1968) 347–350.

S. H. Yalkowsky, S. C. Valvani, Solubility and partitioning. I. Solubility of nonelectrolytes in water. J. Pharm. Sci. 69 (1980) 912–922.

N. Jain, S. H. Yalkowsky, Estimation of the aqueous solubility I: Application to organic nonelectrolytes, J. Pharm. Sci. 90 (2001) 234–252.

C. Hansch, A. Leo, Exploring QSAR—Fundamentals and Applications in Chemistry and Biology, American Chemical Society, Washington, 1995.

J. Sangster, Octanol-Water Partition Coefficients: Fundamentals and Physical Chemistry, Wiley, Chichester, 1997.

P. Buchwald, N. Bodor, Octanol-water partition: searching for predictive models. Curr. Med. Chem. 5 (1998) 353–380.

E. M. Duffy, W. L. Jorgensen, Prediction of Properties from Simulations: Free Energies of Solvation in Hexadecane, Octanol, and Water. J. Am. Chem. Soc.122 (2000) 2878–2888.

A. R. Katritzky, Y. Wang, T. Tamm, M. Karelson, QSPR Studies on Vapor Pressure, Aqueous Solubility, and the Prediction of Water-Air Partition Coefficients, J. Chem. Inf. Comput. Sci. 38 (1998) 720–725.

J. Huuskonen, Estimation of Aqueous Solubility for a Diverse Set of Organic Compounds Based on Molecular Topology, J. Chem. Inf. Comput. Sci. 40 (2000) 773–777.

R. Kühne, R.-U. Ebert, F. Kleint, G, Schmidt, G. Schüürrmann, Group Contribution Methods to Estimate Water Solubility of Organic Chemicals, Chemosphere 30 (1995) 2061–2077.

G. Klopman, H. Zhu, Estimation of Aqueous Solubility of Organic Molecules by the Group Contribution Approach, J. Chem. Inf. Comput. Sci. 41 (2001) 439–445.

L. H. Hall, L. B. Kier, Electrotopological State Indices for Atom Types: A Novel Combination of Electronic, Topological, and Valence State Information, J. Chem. Inf. Comput. Sci. 35 (1995) 1039–1045.

J. M. Sutter, P. C. Jurs, Prediction of Aqueous Solubility for a Diverse Set of Heteroatom-Containing Organic Compounds Using a Quantitative Structure-Property Relationship. J. Chem. Inf. Comput. Sci. 36 (1996) 100–7.

B. E. Mitchell, P. C. Jurs, Prediction of aqueous solubility of organic compounds from molecular structure. J. Chem. Inf. Comput. Sci. 38 (1998) 489–496.

N. R. McElroy, P. C. Jurs, Prediction of Aqueous Solubility of Heteroatom-Containing Organic Compounds from Molecular Structure. J Chem Inf Comput Sci. 2001 September–October; 41(5): 1237–47

P. D. T. Huibers, A. R. Katritzky, Correlation of the Aqueous solubility of Hydrocarbons and Halogenated Hydrocarbons with Molecular Structure, J. Chem. Inf. Comput. Sci. 38 (1998) 283–292.

M. H. Abraham, J. Le, The Correlation and Prediction of the Solubility of Compounds in Water Using an Amended Solvation Energy Relationship, J. Pharm. Sci. 89 (1999) 868–880.

W. M. Meylan, P. H. Howard, Estimating log P with atom/fragments and water solubility with log P, Perspect. Drug Discov. Des. 19 (2000) 67–84.

Xia X, Maliski E, Cheetham J, Poppe L., Solubility prediction by recursive partitioning. Pharm Res. 2003 October; 20(10):1634–40.

Jorgensen W L, Duffy E M., Prediction of drug solubility from structure. Adv Drug Deliv Rev. 2002 Mar. 31; 54(3):355–66.

Eros D, Keri G, Kovesdi I, Szantai-Kis C, Meszaros G, Orfi L., Mini Rev Med Chem. 2004 February; 4(2):167–77. Comparison of predictive ability of water solubility QSPR models generated by MLR, PLS and ANN methods.

Wesson L, Eisenberg D., Protein Sci. 1992 February; 1(2): 227–35. Atomic solvation parameters applied to molecular dynamics of proteins in solution.

Jorgensen W L, Duffy E M., Bioorg Med Chem Lett. 2000 Jun. 5; 10(11):1155–8. Prediction of drug solubility from Monte Carlo simulations.

Abagyan R, Totrov M., J Mol Biol. 1994 Jan. 21; 235(3): 983–1002. Biased probability Monte Carlo conformational searches and electrostatic calculations for peptides and proteins.

STATEMENT REGARDING FEDERALLY SPONSORED RESEARCH AND DEVELOPMENT

Not applicable

BACKGROUND OF THE INVENTION

The invention relates to computational methods of physical chemistry. Specifically, the invention relates to the prediction of solubility of chemical compounds.

Prediction of solubility can be very important in the projects where a decision on synthetic routes considers many options: in these cases a range of reaction schemes and building blocks can be narrowed down considerably on the basis of theoretical predictions of solubility prior to incurring the costs of synthesis and testing, and modifications to improve the solubility could be incorporated into the next design cycle. It is particularly important in the pharmaceutical industry, since it currently is the biggest consumer of high content chemical libraries. Prediction of solubility for drug-like compounds presents a challenge, since these compounds are usually feature-rich, i.e. they contain a number of different features or pharmacophores. A compound's solubility is represented as log S, where S is the concentration of the compound in mol/l for a saturated water solution in equilibrium with the most stable form of the crystalline material.

The thermodynamic equilibrium between a compound's solid phase and saturated aqueous solution can be decomposed into two steps: 1) sublimation of the solid and transfer of the gaseous compound into water, or 2) melting of the crystal and transfer of the liquid to water. Based on the latter thermodynamic cycle, Irmann approximated the difference in log S between a solid and neat liquid as $-\Delta S_m(T_m-T)/2.3RT \approx -0.01(t_m-25)$ at 25° C., where $\Delta S_m$ is the entropy of melting at the melting point, $T_m = t_m + 273.15$ K (F. Irmann, Eine einfache korrelation zwischen wasserloslichkeit und strukture von kohlenwasserstoffen und halogenkohlenwasserstoffen. Chem. Ing. Tech. 37 (1965) 789–798.), while Hansch et al. found that log S for liquid organic compounds in water is linearly related to the compound's octanol/water partition coefficient, log $P_{o/w}$ (C. Hansch, J. E. Quinlan, G. L. Lawrence, Linear free energy relationship between partition coefficients and the aqueous solubility of organic liquids, J. Org. Chem. 33 (1968) 347–350). Yalkowsky et al. combined these results to estimate the solubility of solid nonelectrolytes via equation 1 (S. H. Yalkowsky, S. C. Valvani, Solubility and partitioning. I. Solubility of nonelectrolytes in water. J. Pharm. Sci. 69 (1980) 912–922. [8] N. Jain, S. H. Yalkowsky, Estimation of the aqueous solubility I: Application to organic nonelectrolytes, J. Pharm. Sci. 90 (2001) 234–252).

$$\log S = 0.5 - \log P_{o/w} - 0.01(t_m - 25) \quad (1)$$

Equation 1 usually gives predictions with root mean square (rms) errors=0.7–0.8 log unit. However, it is usually not useful in most projects because it requires experimental knowledge of the compound's melting point. A number of methods exist for estimating log $P_{o/w}$ (C. Hansch, A. Leo, Exploring QSAR—Fundamentals and Applications in Chemistry and Biology, American Chemical Society, Washington, 1995; J. Sangster, Octanol-Water Partition Coefficients: Fundamentals and Physical Chemistry, Wiley, Chichester, 1997; P. Buchwald, N. Bodor, Octanol-water partition: searching for predictive models. Curr. Med. Chem. 5 (1998) 353–380; E. M. Duffy, W. L. Jorgensen, Prediction of Properties from Simulations: Free Energies of Solvation in Hexadecane, Octanol, and Water. J. Am. Chem. Soc. 122 (2000) 2878–2888). This is not the case for melting points. The melting point is determined by the cohesive interactions in the solid phase, and its estimation is essentially as difficult as the one of a compound's solubility.

The principal computational approaches for solubility prediction have been based on group contributions (GC), multiple linear regression (MLR) analysis, and neural networks (NN).

Group Contributions. In this approach, contributions $a_i$ are assigned for the number of occurrences $n_i$ of a structural fragment i in the molecule of interest. The solubility is then calculated as follows.

$$\log S = \sum_i a_i n_i + a_0 \quad (2)$$

The values of group contributions are optimized using from regression analyses; however, the $n_i$ are normally integers and the descriptors are strictly structural fragments in the GC approach. Kühne et al. compared four prior GC algorithms and also developed their own (R. Kühne, R.-U. Ebert, F. Kleint, G, Schmidt, G. Schüürrmann, Group Contribution Methods to Estimate Water Solubility of Organic Chemicals, Chemosphere 30 (1995) 2061–2077). Their dataset consists of experimental data on 351 organic liquids and 343 solids, which are mostly hydrocarbons, halocarbons, polychlorinated biphenyls (PCBs), and monofunctional organic molecules. The number of fragments and correction terms is about 50 in the optimized model. On this dataset it yield absolute average errors of 0.4–0.5 log unit. The standard deviation (rms error) was not reported, but is normally 20–25% higher, i.e. 0.5–0.6 log unit.

The number of fragment types in these early methods was not large enough to treat drug-like molecules well. In the work from Klopman and Zhu (G. Klopman, H. Zhu, Estimation of Aqueous Solubility of Organic Molecules by the Group Contribution Approach, J. Chem. Inf. Comput. Sci. 41 (2001) 439–445) an expanded training set was used. Although the set was still depleted of feature-rich molecules, it consisted of more then 1000 organic chemicals covering a variety of chemical classes and included some complex drugs. The work used 171 fragments and yielded a correlation with $r^2=0.95$ and rms error=0.49 log unit. Using a transformed equation, which introduces non-linearity, the authors were able to obtain a similar fit with reduction in the number of fragments to 118. The modified procedure was tested on a subsequent set of 120 compounds and yielded a rms error of 0.79 log unit.

Multiple Linear Regression. In this method the solubility is calculated as follows:

$$\log S = \sum_i a_i c_i + a_0 \quad (3)$$

$c_i$ are descriptors for the given structure. The coefficients $a_i$ are determined by regression analysis to maximize the correlation coefficient $r^2$ between the training set of log S values and computed results. Typical descriptors include molecular weight, solvent-accessible surface area (SASA), counts of potential donor and acceptor hydrogen bonds in aqueous solution (HBDN, HBAC), counts of specific functional groups and rotatable bonds, electrostatic potential data from quantum mechanical calculations, and a wide-range of topological and electronic indices such as those of Hall and Kier (L. H. Hall, L. B. Kier, Electrotopological State Indices for Atom Types: A Novel Combination of Electronic, Topological, and Valence State Information, J. Chem. Inf. Comput. Sci. 35 (1995) 1039–1045).

There are a number of MLR studies for prediction of aqueous solubility (W. L. Jorgensen, E. M. Duffy, Prediction of Drug Solubility from Monte Carlo Simulations, Bioorg. Med. Chem. Lett. 10 (2000) 1155–1158; A. R. Katritzky, Y. Wang, T. Tamm, M. Karelson, QSPR Studies on Vapor Pressure, Aqueous Solubility, and the Prediction of Water-Air Partition Coefficients, J. Chem. Inf. Comput. Sci. 38 (1998) 720–725; J. Huuskonen, Estimation of Aqueous Solubility for a Diverse Set of Organic Compounds Based on Molecular Topology, J. Chem. Inf. Comput. Sci. 40 (2000) 773–777; J. M. Sutter, P. C. Jurs, Prediction of Aqueous Solubility for a Diverse Set of Heteroatom-Containing Organic Compounds Using a Quantitative Structure-Property Relationship. J. Chem. Inf. Comput. Sci. 36 (1996) 100–7; B. E. Mitchell, P. C. Jurs, Prediction of aqueous solubility of organic compounds from molecular structure. J. Chem. Inf. Comput. Sci. 38 (1998) 489–496; N. R. McElroy, P. C. Jurs, Prediction of Aqueous Solubility of Heteroatom-Containing Organic Compounds from Molecular Structure. J. Chem. Inf. Comput. Sci. 40 (2001), in press; P. D. T. Huibers, A. R. Katritzky, Correlation of the Aqueous solubility of Hydrocarbons and Halogenated Hydrocarbons with Molecular Structure, J. Chem. Inf. Comput. Sci. 38 (1998) 283–292; M. H. Abraham, J. Le, The Correlation and Prediction of the Solubility of Compounds in Water Using an Amended Solvation Energy Relationship, J. Pharm. Sci. 89 (1999) 868–880; W. M. Meylan, P. H. Howard, Estimating log P with atom/fragments and water solubility with log P, Perspect. Drug Discov. Des. 19 (2000) 67–84). The study described in reference (N. R. McElroy, P. C. Jurs, Prediction of Aqueous Solubility of Heteroatom-Containing Organic Compounds from Molecular Structure. J Chem Inf Comput Sci. 2001 September–October; 41(5):1237–47) used a MLR model with 7 descriptors, $r^2=0.72$ and rms=0.75 log unit for the training set and $r^2=0.66$ and rms=0.80 log unit for the test set. The MLR studies of Katritzky and co-workers used a larger initial pools of >800 descriptors and restricted datasets (A. R. Katritzky, Y. Wang, T. Tamm, M. Karelson, QSPR Studies on Vapor Pressure, Aqueous Solubility, and the Prediction of Water-Air Partition Coefficients, J. Chem. Inf. Comput. Sci. 38 (1998) 720–725; P. D. T. Huibers, A. R. Katritzky, Correlation of the Aqueous solubility of Hydrocarbons and Halogenated Hydrocarbons with Molecular Structure, J. Chem. Inf. Comput. Sci. 38 (1998) 283–292). For 411 CHXNO compounds, they obtained $r^2=0.88$ and rms=0.57 with a six-descriptor model (A. R. Katritzky, Y. Wang, T. Tamm, M. Karelson, QSPR Studies on Vapor Pressure, Aqueous Solubility, and the Prediction of Water-Air Partition Coefficients, J. Chem. Inf. Comput. Sci. 38 (1998) 720–725). Huuskonen has also used topological and electronic descriptors for a diverse set of 1297 organic molecules including a good sampling of drugs. (J. Huuskonen, Estimation of Aqueous Solubility for a Diverse Set of Organic Compounds Based on Molecular Topology, J. Chem. Inf. Comput. Sci. 40 (2000) 773–777). This analysis yielded a regression equation with 30 descriptors, $r^2=0.89$ and rms=0.67. Abraham and Le (M. H. Abraham, J. Le, The Correlation and Prediction of the Solubility of Compounds in Water Using an Amended Solvation Energy Relationship, J. Pharm. Sci. 89 (1999) 868–880) used a six-descriptor model, which yielded $r^2=0.92$ and rms=0.56 for 594 molecules. Amino acids, sugars and dicarboxylic acids were not included in their training set. The accuracy is good and the model is laudable for use of a small number of physically significant descriptors, specifically, the molar refractivity $R_2$, dipolarity $\pi_2^H$, hydrogen-bond acidity $\Sigma\alpha_2^H$, hydrogen-bond basicity $\Sigma\beta_2^H$, and volume $V_x$. $\Sigma\alpha_2^H$ and $\Sigma\beta_2^H$ are similar to HBDN and HBAC. The model also contains the product $\Sigma\alpha_2^H \times \Sigma\beta_2^H$, which was introduced to reflect cohesive hydrogen-bonding interactions in the solid state. Meylan and Howard have reported results for regression analyses on large data sets for log S (W. M. Meylan, P. H. Howard, Estimating log P with atom/fragments and water solubility with log P, Perspect. Drug Discov. Des. 19 (2000) 67–84). Their equation uses log $P_{o/w}$ and molecular weight (MW) as descriptors along with 15 correction factors, $f_i$, with various sub-rules to modify the results mostly for the presence of specific functional groups. The equation was developed using experimental log $P_{o/w}$ data; however, computed values for log $P_{o/w}$ can be used and for a set of 3000 compounds, the method yielded $r^2=0.84$ and rms=0.90. Jorgenson and Duffy computed a few physically significant descriptors (W. L. Jorgensen, E. M. Duffy, Prediction of Drug Solubility from Monte Carlo Simulations, Bioorg. Med. Chem. Lett. 10 (2000) 1155–1158) for 150 organic molecules including about 70 drugs by performing a Monte Carlo (MC) statistical mechanics simulation for each solute in water. Eleven descriptors were averaged, most notably the average solute-water Coulomb and van der Waals (ESXL) interaction energies, volume, solven accessible surface area (SASA) and its hydrophobic, hydrophilic and aromatic components, and the hydrogen-bond counts, HBDN and HBAC. The regression equation (equation 4) has five terms and yields $r^2=0.88$, $q^2=0.87$, and rms=0.72.

$$\log S = 0.32 ESXL + 0.65 HBAC + 2.19 \#amine - 1.76 \#nitro - 162 HBAC \cdot HBDN^{1/2}/SASA + 1.18 \qquad (4)$$

A number of product terms were explored to describe the cohesive interactions in the solid state and the one represented in equation 4 is the most significant.

Recursive Partitioning. There is an example in the literature (Xia X, Maliski E, Cheetham J, Poppe L., Solubility prediction by recursive partitioning. Pharm Res. 2003 October; 20(10):1634–40) where a solubility model was built using a recursive partitioning decision tree classification with a training set of 1992 compounds. The model is based on a series of calculated topologic and physical properties of the molecule of interest. The predictive ability of the decision tree was evaluated on a test set of 2851 compounds. The compounds were classified into soluble and insoluble. An experimental test of the prediction showed that the successful selection rate improved from 25% to 50% as compared with the use of a simple cLogP cutoff.

Neural Networks. There are a number of works in the literature, which use computational neural networks to predict solubility (J. Huuskonen, M. Salo, J. Taskinen, Aqueous Solubility Prediction of Drugs Based on Molecular Topology and Neural Network Modeling, J. Chem. Inf. Comput. Sci. 38 (1998) 450–456; J. Huuskonen, Estimation of Aqueous Solubility for a Diverse Set of Organic Compounds Based on Molecular Topology, J. Chem. Inf. Comput. Sci. 40 (2000) 773–777; J. M. Sutter, P. C. Jurs, Prediction of Aqueous Solubility for a Diverse Set of Heteroatom-Containing Organic Compounds Using a Quantitative Structure-Property Relationship. J. Chem. Inf. Comput. Sci. 36 (1996) 100–7; B. E. Mitchell, P. C. Jurs, Prediction of aqueous solubility of organic compounds from molecular structure. J. Chem. Inf. Comput. Sci. 38 (1998) 489–496; N. R. McElroy, P. C. Jurs, Prediction of Aqueous Solubility of Heteroatom-Containing Organic Compounds from Molecular Structure. J Chem Inf Comput Sci. 2001 September–October; 41(5): 1237–47). The NN approach has its advantages and disadvantages, an often the predictive ability of the NN is not better than that of MLR. Huuskonen (J. Huuskonen, Estimation of Aqueous Solubility for a Diverse Set of Organic Compounds Based on Molecular Topology, J. Chem. Inf. Comput. Sci. 40 (2000) 773–777) developed MLR and NN models using 884 diverse organic molecules and drugs for training with the Hall and Kier descriptors (L. H. Hall, L. B. Kier, Electrotopological State Indices for Atom Types: A Novel Combination of Electronic, Topological, and Valence State Information, J. Chem. Inf. Comput. Sci. 35 (1995) 1039–1045). For a test set of 413 molecules, the results were $r^2$ (rms) values of 0.88 (0.71) and 0.92 (0.60) for the two models.

A good review of solubility prediction methods can be found in reference (Jorgensen W L, Duffy E M., Prediction of drug solubility from structure. Adv Drug Deliv Rev. 2002 Mar. 31; 54(3):355–66).

A fairly comprehensive review of water solubility prediction methods is presented in reference (Eros D, Keri G, Kovesdi I, Szantai-Kis C, Meszaros G, Orfi L., Mini Rev Med Chem. 2004 February; 4(2):167–77. Comparison of predictive ability of water solubility QSPR models generated by MLR, PLS and ANN methods). The authors have selected 1381 compounds from scientific publications in a unified database and used this dataset in the calculations. The models were based on calculated descriptors only. Multiple linear regression analysis (MLR), partial least squares method (PLS) and artificial neural network (ANN) models were developed. Standard error of prediction of the best model generated with ANN (with 39-7-1 network structure) was 0.72 in log S units while the cross validated squared correlation coefficient (Q(2)) was better than 0.85.

BRIEF SUMMARY OF THE INVENTION

In one embodiment, the invention comprises a method of estimating the solubility of a compound. In this method descriptors of cohesive interactions in the solid state are calculated from a computational model of a solid state, i.e. from a small cluster of copies of the molecule of interest assembled using a molecular mechanics method. A model for predicting solubility is built using the cohesive interaction descriptors along with other descriptors useful for this purpose. Predicted solubility is computed for the compound of interest by computing the same descriptors and applying the solubility model. Explicit modeling of solid state allows to more accurately characterize cohesive interactions in solids, hence, more accurately predict solubility.

BRIEF DESCRIPTION OF THE SEVERAL VIEWS OF THE DRAWINGS

FIG. 1 shows the correlation of predicted and experimental log S values for the ACD method.

FIG. 2 shows the correlation of predicted and experimental log S values for the described method.

DETAILED DESCRIPTION OF THE INVENTION

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Monte Carlo (MC) simulations in torsional angle space (Abagyan R, Totrov M., J Mol Biol. 1994 Jan. 21; 235(3): 983–1002. Biased probability Monte Carlo conformational searches and electrostatic calculations for peptides and proteins) are used to build a model of the solid phase of compounds. In each simulation four copies of a molecule are assembled into a cluster by running an MC energy optimization in vacuum with distance restraints imposed on the molecules so that they do not fly away from each other more them 15 Å (the restraints impose a distance-dependent energy penalty if the distance between two molecules is larger then 15 Å). Each run consists of sampling 15,000 MC moves followed by 200 steps of local minimization—total 3 million conformations of a tetramer of a compound. After building the cluster additional 16 copies of the molecule are sequentially docked onto the cluster using fully flexible MC docking. This procedure results in a cluster of 20 copies of the molecule of interest densely packed in a manner similar to the one in the solid state. This model can be used for computing various characteristics of the solid state of the molecule.

In the preferred embodiment a number of descriptors of the solid phase interactions are calculated. Below are the descriptors together with their symbols used in equations.

| | |
|---|---|
| VDW | is van der Waals energy, |
| HB | is hydrogen bond interaction energy, |
| TO | is torsion angle strain energy, |
| DeltaHB | is the difference between hydrogen bond interaction energies in the solid phase and in solution, |
| NoRot | is the number of rotatable bonds, |
| NoRotWs | is the number of rotatable bonds without symmetrical groups. |

The energy descriptors were calculated for every molecule in the core tetramer and averaged.

In this embodiment the solution phase was modeled by sequential MC docking of 50 water molecules onto an energy minimized molecule of a solute.

Below are the descriptors calculated for the solution phase together with their symbols used in equations.

| | |
|---|---|
| ASE | is solvation energy calculated via atomic solvation model (Wesson L, Eisenberg D., Protein Sci. 1992 Feb; 1(2): 227–35. Atomic solvation parameters applied to molecular dynamics of proteins in solution), |
| STE | is surface tension solvation energy (12 cal/ Å$^2$), |
| PEE | is Poisson electrostatics, |
| PSA | is polar surface area, |
| SA | is surface area, |
| clogP | is calculated octanol/water partition coefficient, |
| MW | is molecular weight. |

The model was built and validated on the set of molecules from reference (Jorgensen W L, Duffy E M., Bioorg Med Chem Lett. 2000 Jun. 5; 10(11):1155–8. Prediction of drug solubility from Monte Carlo simulations). This set included the following molecules:

acetaminophen, alanine, allopurinol, aspirin, atropine, barbital, benzocaine, bifonazole, bromazepam, caffeine, chloroamphenicol, chlorpromazine, cocaine, codeine, corticosterone, desipramine, valium, diethylstilbestrol, ephedrine, estradiol, ethyl-4-hydroxybenzoate, fenbufen(Lederfen), flurbiprofen, griseofulvin, hydrocortisone, ibuprofen, imipramine, indomethacine, ketoprofen, lidocaine, lorazepam, morphine, naproxen, nifedipine, nifuroxime, nitrofurantoin, oxazepam, perphenazine, phenacetin, Phenobarbital, phenytoin, prednisone, procaine, progesterone, promazine, prostaglandin E2, salicylic acid, sulindac, testosterone, theophylline, thioridazine, trifluorperazine, triflupromazine, warfarin.

The descriptors calculated for this set of drug molecules were used to derive regression equations to predict solubility. An exhaustive search in the equation space was performed, i.e. all possible combinations of descriptors were tested. The three best performing equations are as follows:

$$\text{Log } S = 1.243 + VDW^*0.0421 + NoRotWs^*0.202 - PSA^*0.0126 - SA^*0.0055 - c \log P^*0.638$$

$$\text{RMSE}=0.569, R^2=0.837, \text{XRMSE}=0.646, \text{XR}^2=0.792 \quad (5)$$

$$\text{Log } S = 0.94 + VDW^*0.0443 + NoRot^*0.182 - PSA^*0.0116 - SA^*0.00545 - c \log P^*0.626$$

$$\text{RMSE}=0.558, R^2=0.844, \text{XRMSE}=0.634, \text{XR}^2=0.799 \quad (6)$$

Log $S=1.068+(VDW+HB+TO)*0.0482-\text{No-Rot}*0.187-PSA*0.0115-SA*0.00568-c \log P*1.6$ $$\text{RMSE}=0.557, R^2=0.844, \text{XRMSE}=0.634, XR^2=0.799 \quad (7)$$

RMSE is the root mean square standard error,
$R^2$ is the correlation coefficient,
XRMSE is the root mean square standard error cross validated by leave-one-out method,
$XR^2$ is the cross validated correlation coefficient.

This set of molecules was also used in order to compare the performance of the described method with a widely used method commercially available from ACD Labs. The method uses the following equation:

$$\text{Log } S=0.92-c \log P*0.834-MW*0.0084 \quad (8)$$

The performance of the ACD method was much worse and yielded RMSE=1.09. The performance of the ACD method is compared with the described method on FIGS. 1 and 2.

What is claimed is:

1. A method of predicting solubility of a chemical compound comprising the steps of:
  a. identifying an electronically stored library of chemical molecules;
  b. building a computational model of a solid state of a molecule from said library by assembling a cluster of three or more copies of said molecule using a molecular mechanics method;
  c. computing energy, packing and interaction parameters from said model;
  d. computing other descriptors useful for predicting solubility of said molecule;
  e. repeating steps (b), (c) and (d) for every molecule from said library;
  f. building a solubility model using a quantitative method, which uses the parameters and descriptors computed in steps (c), (d) and (e);
  g. repeating steps (b), (c) and (d) for said compound;
  h. computing predicted solubility of said compound using said model and parameters and descriptors computed for said compound in steps (c), (d) and (e).

2. The method of claim 1, wherein step (b) includes copes of solvent molecules in addition to copies of said molecule.

3. The method of claim 1, wherein protonation state of copies of said molecule is dynamically recalculated during building a model of a solid state.

* * * * *